United States Patent [19]

Benecke

[11] Patent Number: 5,665,050

[45] Date of Patent: Sep. 9, 1997

[54] APPARATUS FOR MEDICAL ENDOSCOPY WITH A SUPERELASTIC ELEMENT AND METHOD OF MAKING THE SAME

[75] Inventor: Rainer Benecke, Todendorf, Germany

[73] Assignee: Olympus Winter & Ibe GmbH, Hamburg, Germany

[21] Appl. No.: 620,943

[22] Filed: Mar. 22, 1996

[30] Foreign Application Priority Data

Mar. 25, 1995 [DE] Germany .................. 195 10 962.7

[51] Int. Cl.$^6$ ........................................ A61B 1/00
[52] U.S. Cl. .................. 29/456; 600/143; 600/151; 606/205; 128/151; 148/563; 148/565; 219/121.69; 219/121.73; 219/121.85
[58] Field of Search .................. 606/205, 206, 606/207, 174, 170, 281; 128/751; 600/143, 151; 148/565, 564, 563

[56] References Cited

U.S. PATENT DOCUMENTS

| 4,708,750 | 11/1987 | Field et al. ............... | 148/565 X |
| 5,282,806 | 2/1994 | Haber et al. ............. | 606/205 X |

FOREIGN PATENT DOCUMENTS

WO92/05828  4/1992  WIPO .................. 604/281

Primary Examiner—Beverly M. Flanagan
Attorney, Agent, or Firm—Walter C. Farley

[57] ABSTRACT

A medical endoscope has a superelastic-alloy force-transmitting element having at least one recess in its surface at a coupling site and being positively connected to a load-receiving component, the recess being formed by sublimation removal of material.

6 Claims, 2 Drawing Sheets

APPARATUS FOR MEDICAL ENDOSCOPY WITH A SUPERELASTIC ELEMENT AND METHOD OF MAKING THE SAME

FIELD OF THE INVENTION

The invention relates to a medical endoscopy apparatus with a force-transmitting component of a superelastic material, and to a positive connection between the component of superelastic material and a cooperating element.

BACKGROUND OF THE INVENTION

Several suitable superelastic alloys are known for use in medical devices particularly Nickel Titanium (Ni-Ti) alloys. These alloys find many applications in medicine They are bio-compatible and exhibit shape-memory characteristics applicable for many purposes. Regarding the objectives of the present invention, the materials are characterized by their superelastic properties whereby, upon being mechanically loaded, a shape change up to about 8% at constant applied force is possible. Accordingly, these alloys may be used as force-transmitting components which may be substantially deformed without rupturing or which illustratively are used as force-limiting means in the manner described in the German patent document Cl 43 13 903.

However, certain manufacturing problems are obstacles when wishing to use the superelastic alloys on a wider scale for the purposes above. In the state of the art as known to-date, and as stated in the above patent document, the manufacture of superelastic alloys requires complex adjustment of the accurate phase state. Moreover, the alloy composition must be quite rigorous, and entails costly manufacturing. Conventional subsequent working is hardly feasible.

As regards the described pull rod 6 (FIG. 1) of the above cited document, problems arise in coupling the load-receiving components 5, 10 to the ends of said element. These coupling sites can be made in the state of the art only if the pull rod was fitted at the factory with prefabricated coupling sites and if they were thermally pretreated. The state of the art precludes using segments of spool-fed wire that would be highly economical.

If segments of superelastic alloy spool-fed wire were used, they could not be worked. Because of the material's superelastic properties, cold-forming or milling are impossible. Additionally, it is impossible to solder these alloys and achieve adequate soldering strength. Welding is excluded because of thermal stress.

All attempts for post-working superelastic alloys have remained unsuccessful or entail mechanical or thermal stressing of the alloy, destroying its superelastic properties and furthermore degrading the material strength. After such treatment, the material will break upon subsequent stressing.

Thus, in the state of the art, force-transmitting elements of superelastic materials must be manufactured in their final shape using the required procedure appropriate to the alloy and working after that procedure is precluded. As a result, the manufacturing costs are very high. Using cheaper spool-fed material is impossible.

SUMMARY OF THE INVENTION

Accordingly, an object of the present invention is to provide an apparatus of the type described above which allows economical manufacture.

Briefly described, the invention comprises an apparatus for medical endoscopy with a superelastic-alloy, force-transmitting element and a load-receiving component. A positive connection between said force-transmitting element and said load-receiving component is accomplished by forming at least one recess at a coupling site on the element, the at least one recess being formed by sublimation removal of material.

It was surprisingly discovered that recesses can be made in the surfaces of superelastic alloys by removal of material by sublimation without thereby affecting the material properties. Recesses may be configured to be suitable for geometric locking, typically in a positive manner. Accordingly, superelastic-alloy spool-fed wire may be used with the result that manufacturing of such devices can be made substantially more economical. For instance, superelastic-alloy spool-fed wires or long tubes may be cut to size and can then be fitted with recesses at their surfaces at the required coupling sites, these recesses making possible a wide variety of positively locking, high-strength connections to attach load-receiving components.

The expression "sublimation removal" denotes removal of material by sublimation. The physical concept of "sublimation" denotes a process wherein the material passes directly from a solid phase into the gaseous phase, an example being frozen water on cold winter days sublimating directly from the ice phase into water vapor. Sublimation is characterized by the absence of an intermediate liquid phase which is otherwise usual in evaporation processes.

Sublimation removal may take place by appropriate energy incidence on the material, for instance using electron beams or the like. It is critical that sublimation alone take place, that is, that upper or outer layers of the material be heated rapidly in such a manner that they evaporate directly without unduly heating the material underneath which otherwise would be unduly thermally stressed. The material will not melt in this process. Thus, no liquid phase occurs which would strongly thermally affect the material and thereby entail marked changes in the complex crystal configuration of the superelastic alloy.

Sublimation by laser irradiation offers the advantage of low equipment expenditure. Thus, for example, a vacuum chamber is unnecessary. Moreover laser processing allows producing exceedingly fine micro-structures such as may be required for very fine endoscopic instruments.

When the recess is made in the form of a helical thread, the positively-locking connection may be in the form a threaded connection and thereby will be compatible with conventional designs.

A squeezed or crimped connection may implemented by forces merely sufficient to implement the positive locking, while too low to unduly stress the superelastic material.

DESCRIPTION OF THE PREFERRED EMBODIMENTS

Figure 1:
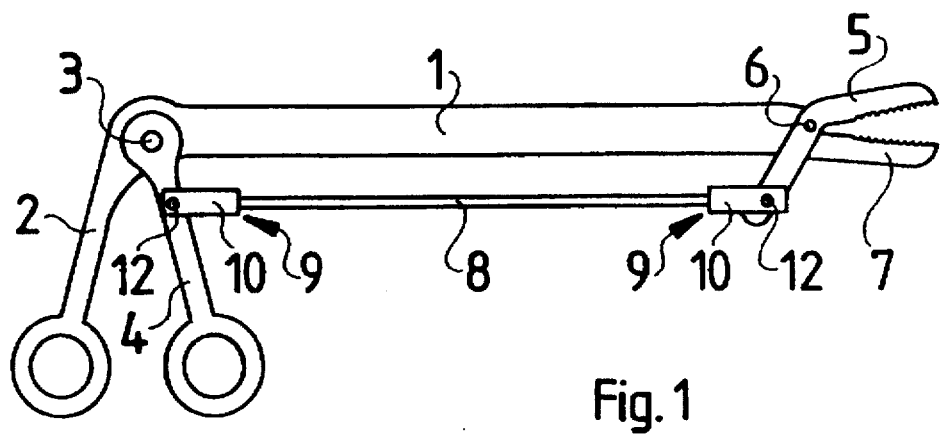
FIG. 1 is a schematic side elevation of endoscopic forceps with a superelastic force-transmitting element having two coupling sites.

FIG. 1 shows, in a highly schematic manner, endoscopic forceps.

A shank 1 merges at its proximal end into a rigidly affixed shears grip 2. At the distal end of shank 1 is a stationary arm 7 rigidly affixed to the shank 1. A shears grip 4 pivotally linked at a pivot 3 to an upper end of grip 2 is coupled to and controls an arm 5 pivotable about a pivot 6 relative to arm 7.

The force-transmitting element controlling displacement of arm 5 comprises a pull rod 8 made of a superelastic alloy manufactured as a portion of a prefabricated spool-fed wire of indeterminate length. Pull rod 8 is connected at coupling sites 9 at its ends to end coupling members 10 which transmit force either in tension or compression (either pull or push), each comprising a transverse borehole 11 and being pivotally connected by pivot pins 12 to one of the forceps' displaceable shears grips 4 and the displaceable arm 5.

Figure 2:
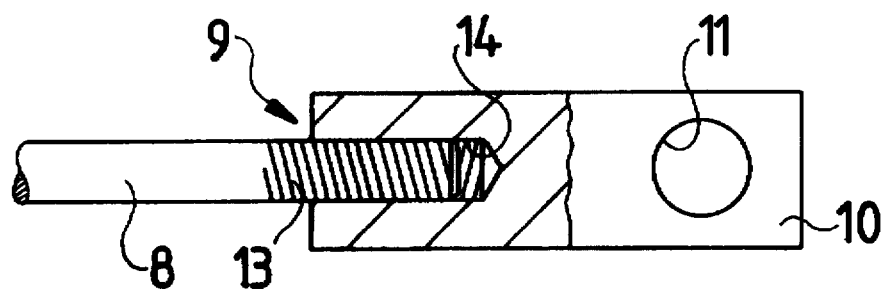
FIG. 2 is an enlarged partial section of one of the coupling sites of FIG. 1.
Figure 3:
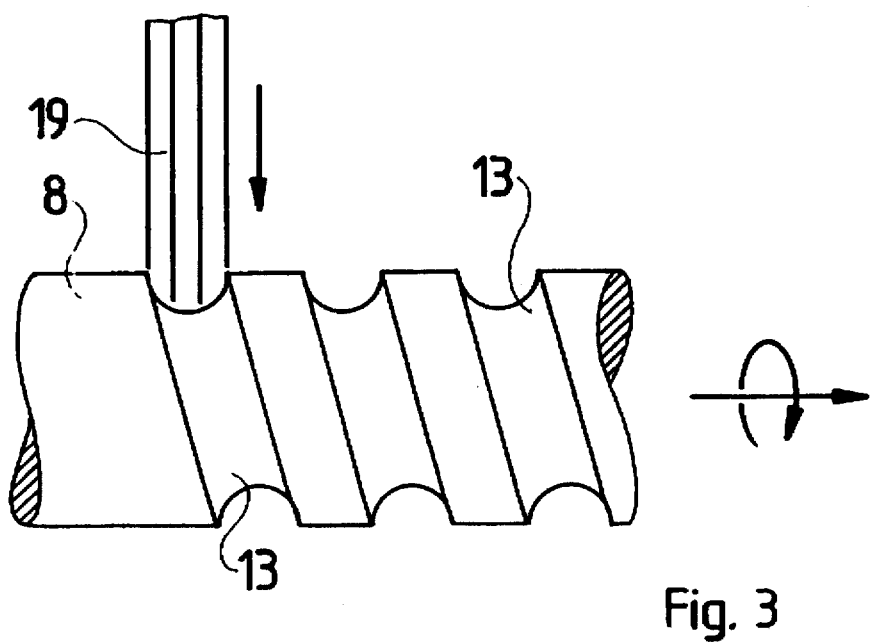
FIG. 3 is an enlarged side view relating to FIG. 2 of the manufacturing of the thread.

To positively lock the coupling sites at the opposite ends of pull rod 8 to the particular coupling members 10, the coupling sites are provided with recesses in their surfaces which, in the embodiment of FIGS. 1–3, take the form of external threads 13. Threads 13 engage a borehole 14 in an end member 10 which has a mating inside thread.

Figure 4:
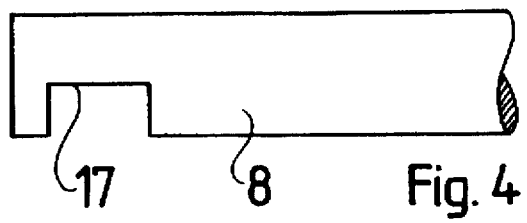
FIGS. 4–7 are detail views of further embodiments of coupling sites shown in front view of FIG. 2.
Figure 5:
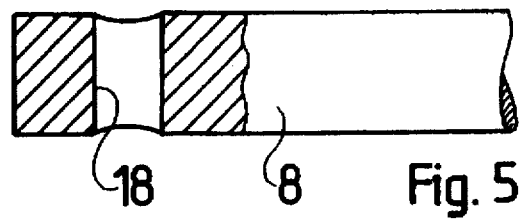
Figure 6:
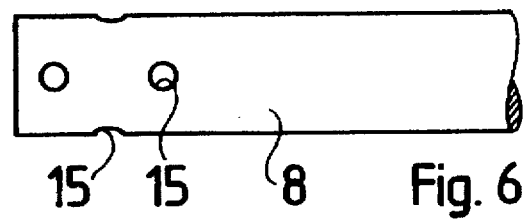
Figure 7:
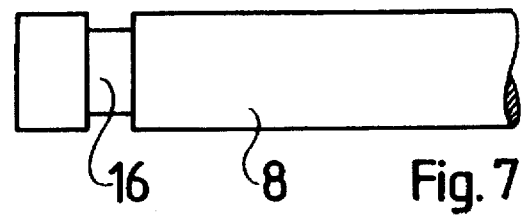

Alternatively, each end member 10 also may be squeezed or crimped onto the threads 13. In this case, the surface recesses at coupling sites 9 may be made in different shapes, such as point recesses 15 as shown in FIG. 6, as a circumferential channel 16 as shown in FIG. 7, as a transverse groove 17 as shown in FIG. 4 or as a transverse through-hole 18 as shown in section in FIG. 5.

The recesses 13, 15, 16, 17 or 18 in the surface of the forceps rod 8 cannot be made conventionally because on one hand suitable solders are unavailable to solder onto superelastic alloys and on the other hand welding is precluded because of excessive thermal stressing and mechanical deformation because of excessive mechanical stresses on the alloy.

As shown in FIG. 3, the surface recess in pull rod 8 in this embodiment is in the form of a thread made by using a focused energy beam 19 pointed at the surface in the direction of the arrow. A laser beam is especially advantageous as the energy beam 19 because it allows operating in an unencumbered free space, that is, without resort to a vacuum chamber. Appropriate optics of a conventional nature, not shown, can be used to achieve fine focus control of the laser beam and also appropriate accuracy and speed control regarding its energy feed whereby only the particular upper layer of the superelastic material is caused to evaporate while the layers below will only be heated relatively moderately, that is, without destroying the superelastic properties. This implementation may be in particular in the form of pulsed application of strong pulses causing only short-term evaporation of the material.

Because of convenience regarding equipment, laser beam 19 of the embodiment of FIG. 3 is stationary, the pull rod 8 being displaced and rotated in the directions of the arrows to produce the helical thread 13.

The recesses shown in the embodiments of FIGS. 4 through 7 may be made in essentially the same manner and, when using laser beams finely focussed by optics, very fine structures such as the circumferential channel 16 of FIG. 7 with a precisely rectangular cross-section can be made so as to be well suited for positively coupling an appropriate load-receiving end member.

Figure 8:
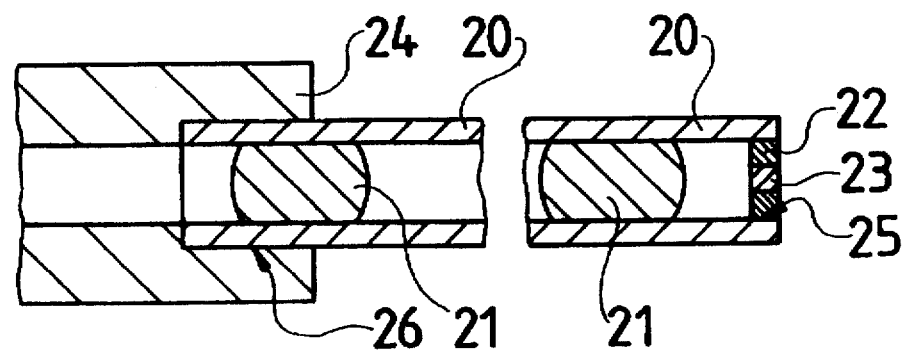
FIG. 8 is a side elevation, in section along a central axis, of a superelastic tube of endoscope optics with two coupling sites.

FIG. 8 shows a further embodiment of the invention wherein the force-transmitting element is a tube 20 which is part of an endoscope optics system. Rod lenses 21 of conventional endoscope optics are mounted in tube 20. A window 23 is fixed in place by an inner ring 22 at the distal end of tube 20. The proximal end of tube 20 is inserted in the borehole of a main housing body 24 of the endoscope, body 24 also comprising an ocular, not shown.

A tube 20 made of a superelastic material offers many advantages in medical applications wherein the tube 20 must transmit high bending stresses. A typical application concerns very long and thin optics by means of which the examining view of a urologist is passed through the urethra as far as the kidney. Typically, such optics are about 40 cm long with a diameter of 3 mm. During insertion, such optics are exposed to high bending stresses which frequently cause destruction, such destruction being averted in accordance with the invention by using superelastic materials.

In such cases adequately reliable affixation of the tube to the coupling sites 25 and 26 is a problem; in the embodiment of FIG. 8, these coupling sites are for inside ring 22 and to the main body 24.

Reliable connections can be established at these coupling sites only by positive locking means, that is, for instance, using a inner thread to hold the inner ring 22 to coupling site 25 and an outer thread at coupling site 26 for affixation to main body 24. If tube 20 is not correspondingly fitted to the superelastic materials in the factory but instead is made from spool-fed tubing, then the threads or other surface recesses used for positive locking may be made by a sublimation technique such as illustrated in FIG. 3.

Furthermore, other endoscope shanks, such as one used over tube 20, may be made of a superelastic material. Coupling sites of such shanks found on main bodies, rinse valves or the like may be processed by sublimation.

Other force-transmitting elements for medical endoscopic devices also can be made in this manner. Illustratively, arm 5 of the endoscopic forceps of FIG. 1 may be made of a superelastic material. The arm may be made by laser sublimating out of a continuous plate by cutting out the blank and then penetrating the cut-out to form boreholes for pivots 6 and 12.

What is claimed is:

1. A method of making a positive connection in a medical instrument between a force-transmitting element and at least one load-receiving component wherein said force-transmitting element is made of a superelastic metal alloy, comprising the steps of sublimating material from the superelastic metal alloy of the force-transmitting element to form a recess therein, shaping the load-receiving component to form a mating part, and coupling said component and element together.

2. A method according to claim 1 wherein the recess in the force transmitting element is formed as a helical external thread and the load-receiving component is shaped with a mating internal thread.

3. A method according to claim 1 wherein the step of sublimating material includes irradiating the material with a laser to evaporate material without causing the material to pass through a liquid state.

4. A method according to claim 1 wherein material is removed to form an annular recess.

5. A method according to claim 1 wherein the step of coupling comprises forming a positive connection by crimping the load-receiving component into the recess in the force-transmitting element.

6. A method according to claim 1 wherein the step of a sublimating includes exposing a selected portion of the force-transmitting element to pulsed laser energy to sublimate the selected portion without the material of the portion entering a liquid phase.

* * * * *